United States Patent [19]

Rasmussen et al.

[11] Patent Number: 5,314,800

[45] Date of Patent: *May 24, 1994

[54] PURIFIED HUMAN CYTOMEGALOVIRUS PROTEIN

[75] Inventors: Lucy E. Rasmussen, Menlo Park; Thomas C. Merigan, Portola Valley, both of Calif.

[73] Assignee: The Board of Trustees of the Leland Stanford Junior University, Stanford, Calif.

[*] Notice: The portion of the term of this patent subsequent to Sep. 5, 2005 has been disclaimed.

[21] Appl. No.: 17,509

[22] Filed: Feb. 12, 1993

Related U.S. Application Data

[63] Continuation of Ser. No. 104,392, Oct. 2, 1987, Pat. No. 5,194,256, which is a continuation of Ser. No. 642,828, Aug. 21, 1984, Pat. No. 4,743,562.

[51] Int. Cl.$^5$ .......................... C12Q 1/70; C12N 5/20; C07K 3/18

[52] U.S. Cl. .................................. 435/4; 435/240.27; 530/413

[58] Field of Search .................. 530/388.3, 389.4, 413; 435/240.27, 4

[56] References Cited

U.S. PATENT DOCUMENTS 4,743,562  5/1988  Rasmussen et al. .
5,194,256  3/1993  Rasmussen et al. .

Primary Examiner—George C. Elliott

[57] ABSTRACT

A purified human CMV virion protein that has a molecular weight of approximately 86,000 daltons by SDS-PAGE and exhibits in vivo. immunizing activity and a murine monoclonal antibody that binds specifically to the protein and exhibits complement-independent human CMV neutralizing activity are described. The antibody is useful for isolating the protein by affinity chromatography and the protein is, in turn, useful for detecting CMV neutralizing antibody in sera and as a vaccine.

4 Claims, 1 Drawing Sheet

PURIFIED HUMAN CYTOMEGALOVIRUS PROTEIN

REFERENCE TO GOVERNMENT GRANT

This invention was made with Government support under grant no. AI-05629 awarded by the National Institutes of Health. The government has certain rights in this invention.

This application is a continuation of application Ser. No. 07/104,392, filed Oct. 2, 1987, now U.S. Pat. No. 5,194,256; which is a continuation of application Ser. No. 06/642,828, filed Aug. 21, 1984, now U.S. Pat. No. 4,743,562.

DESCRIPTION

1. Technical Field

This invention is in the fields of protein chemistry and disease diagnosis and prophylaxis. More particularly it relates to a human cytomegalovirus (CMV) protein that is involved in antibody-mediated CMV neutralization and antibodies that bind specifically to that protein.

2. Background Art

CMV is a member of the betaherpesvirus subfamily of the Herpesviridae family. CMV is medically significant as a cause of congenital anomalies and infection in immunosuppressed individuals.

There are approximately 30 proteins associated with CMV virions and more than 50 proteins expressed by the vital genome in infected cells. Prior investigators have analyzed CMV proteins from virions, dense bodies, and infected cells. Several have reported finding proteins having molecular weights in the range of 80,000–90,000 daltons as determined by gel electrophoresis. See *J. Virology* (1976) 19:243–254; *J. Virology* (1976) 19:594–609; *J. Virology* (1976) 20:604–611; *Virology* (1975) 66:464–473; *J. Gen Virol* (1977) 34:447–454; *Intervirology* (1980) 13:154–161.

Murine monoclonal antibodies to various CMV proteins have been reported. See *Infection and Immunity* (1982) 36:924–932 and 38:273–271 and *J. Clinical Microbiology* (1983) 18:331–343.

Specific CMV proteins that stimulate immunity in humans have not been identified previously. The present invention concerns a CMV protein that exhibits immunizing activity. This protein constitutes only a small fraction of the total viral protein. Because of this it is not an effective immunizing agent when administered in an unisolated (e.g., killed virus) form.

The protein's involvement in CMV neutralization was not discovered through immunoprecipitation tests such as those used in some of the CMV protein studies referenced above. Immunoprecipitation by itself reveals nothing about immunizing activity. Instead the protein was discovered by discovering a monoclonal antibody that neutralizes CMV and using that antibody to target the protein.

DISCLOSURE OF THE INVENTION

One aspect of the invention is a purified human CMV virion protein having:

(a) a molecular weight of approximately 86,000 daltons as determined by sodium dodecyl sulfate-polyacrylamide gel electrophoresis (SDS-PAGE); and (b) in vivo immunizing activity; the protein being substantially free of other CMV proteins, and derivatives of the protein that have said activity.

A second aspect of the invention is a monoclonal antibody that binds specifically to the above described 86,000 dalton protein. The murine monoclonal antibody identified herein as 1G6 and functional equivalents thereof are preferred.

Another aspect of the invention is a method of isolating the above described 86,000 dalton protein from CMV-infected human cells or extracellular CMV virions comprising:

(a) disrupting the cells or virions;

(b) contacting the disruptate with the above described monoclonal antibody immobilized on a solid phase under conditions that permit antigen-antibody binding;

(c) separating unbound disruptate from the solid phase; and (d) eluting the protein from the solid phase.

Another aspect is a method of determining the presence of human CMV neutralizing antibodies in a sample of human Ig-containing body fluid comprising:

(a) incubating the sample with the 86,000 dalton protein or an active fragment thereof under conditions that permit antigen-antibody binding; and (b) detecting the presence of immune complexes that include the 86,000 dalton protein in the incubate.

Murine hybridomas that produce monoclonal antibodies that bind specifically to the 86,000 dalton protein are another aspect of the invention.

Other aspects of the invention are anti-CMV sera produced by immunizing an animal with an effective amount of the 86,000 dalton protein, human CMV vaccines that contain the 86,000 dalton protein or a derivative thereof that has similar immunizing activity as its active ingredient and methods for vaccinating patients with such vaccines.

MODES FOR CARRYING OUT THE INVENTION

A. Definitions

Figure 2:
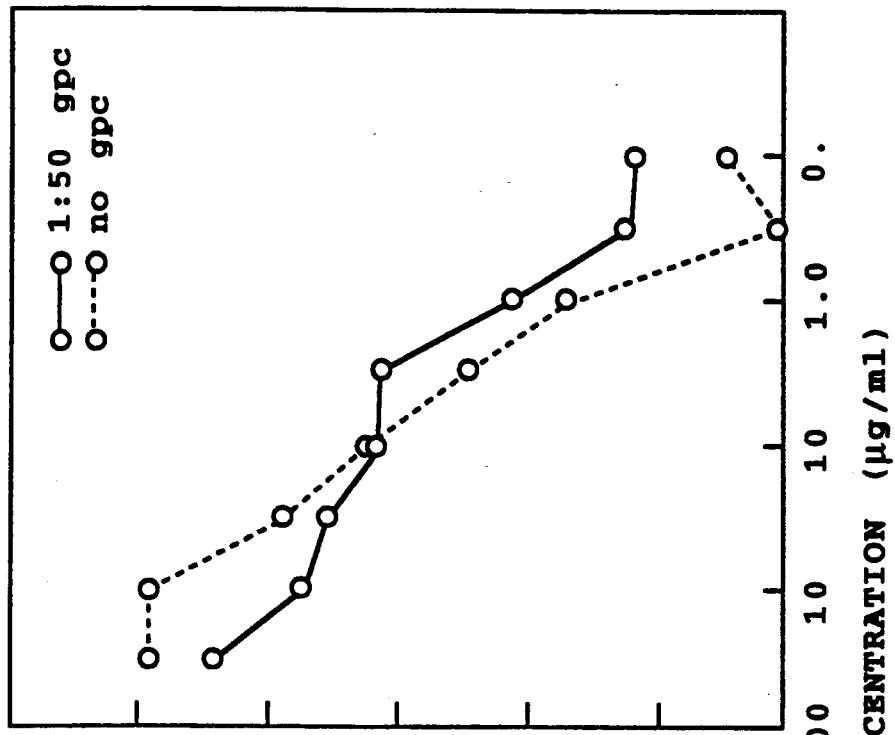
FIGS. 1 and 2 are graphs of the results of the quantitative CMV AD169 neutralization tests using monoclonal antibody 1G6 described in the example, infra.

As used herein the term "immunizing activity" means the ability to induce the production of CMV neutralizing antibodies in vivo.

As used herein the term "neutralizing activity" denotes the ability to affect CMV in a manner that eliminates or substantially attenuates its ability to infect.

As used herein the term "derivative" is intended to include modifications of the native 86,000 dalton protein that retain the immunizing activity of the native 86,000 dalton protein. The term is intended to include, without limitation, fragments, oligomers or complexes of the protein, polypeptides or fusion proteins made by recombinant DNA techniques whose amino acid sequences are identical or substantially identical ( i.e., differ in a manner that does not affect immunizing activity adversely) to that of the protein or that of an active fragment thereof, or that lack or have different substituents (e.g., lack glycosylation or differ in glycosylation), and conjugates of the protein or such fragments, oligomers, polypeptides and fusion proteins and carrier proteins.

As used herein the term "functional equivalent" means a monoclonal antibody that recognizes the same determinant as antibody 1G6 and crossblocks antibody 1G6. It is intended to include antibodies of murine or other origin of the same or different immunoglobulin class, and antigen binding fragments (e.g., Fab, F(ab')$_2$, Fv) of 1G6 and such other antibodies.

B. Characterization of CMV Protein

The novel CMV protein of the invention is not strain specific. Its production has been observed in both laboratory strains of CMV and in clinical CMV isolates. Different strains may, however, produce different amounts of the protein. The native protein is believed to be a glycosylated virion protein that is the product of expression of a single CMV gene. In this regard the 1G6 antibody (described hereinafter) to the protein neutralizes cell free virions. The protein is localized on cytoplasmic organelles of CMV infected cells.

The reduced form (i.e., no disulfide bonds) of the protein has a molecular weight of approximately 86,000 daltons as measured by the electrophoretic mobility of the protein in a linear 7.5% polyacrylamide gel cross-linked with N,N'-methylenebisacrylamide in sodium dodecyl sulfate (SDS-PAGE) as described by Laemmli, U. K., *Nature* (London) (1970) 227:680–685. It is well known that molecular weights so determined are approximate and their values are dependent on the method. The conformation of the protein affects its mobility in the gel system and, therefore, its molecular weight may not be identical as measured by other procedures. The reduced protein appears as a single band in the electrophoretic profile. High molecular weight species appear in the profile when the protein is isolated and resolved under nonreducing conditions. These species may be indicative of oligomeric forms of the protein.

C. Isolation of Protein

A currently preferred method for purifying the 86,000 dalton protein of the invention from CMV infected cells or cell free CMV isolates is affinity chromatography using a monoclonal antibody that binds specifically to the protein.

Monoclonal antibodies to the protein may be made by the somatic cell hybridization techniques described initially by Kohler, B. and Milstein, C., *Nature* (1975) 256:495–497. The procedure involves immunizing a host animal (typically a mouse because of the availability of murine myelomas) with human CMV obtained from infected cultures or with the protein itself. CMV may be grown in human fibroblasts in conventional serum-supplemented liquid growth media such as RPMI 1640 or Dulbecco's minimum essential medium. Virus may be sedimented from culture supernatants by centrifugation.

Antibody-producing cells (e.g., peripheral blood lymphocytes, splenocytes) are taken from the immunized host and mixed with a suitable tumor fusion partner in a liquid growth medium containing a fusogen such as polyethylene glycol of molecular weight 2000 to 5000. After the fusion the cells are washed to remove residual fusion medium and incubated in a selective growth medium (i.e., a growth medium containing additives to which the parent tumor line is sensitive) such as HAT medium. Only hybrid cells that possess the parent non-cancerous cells' ability to survive culture-in the selective medium and the parent tumor cells' immortality survive culture in the selective medium. Surviving hybrids may be expanded and their culture media screened for the presence of anti-CMV antibodies by radio-immunoassay (RIA), a micro-neutralization assay that detects inhibition of viral cytopathic effect (CPE) in cell cultures or other assays that detect anti-vital activity (e.g., plaque reduction). Positive cultures may be screened for their ability to recognize and bind to the 86,000 dalton protein by immunoprecipitating labeled infected cell extracts with the positive cultures and analyzing the precipitate by SDS-PAGE for the presence of a labeled 86,000 dalton component. Hybrids that produce antibody that binds specifically to the protein may be subcloned and grown in vitro or in vivo by known procedures. The antibody may be isolated from the resulting culture medium or body fluid, as the case may be, by conventional procedures for isolating immunoglobulins.

The resulting monoclonal antibody may be covalently coupled to solid supports such as celluloses, polystyrene, polyacrylamide, cross-linked dextran, beaded agarose or controlled pore glass using bifunctional coupling agents that react with functional groups on the support and functional groups (i.e., reactive amino acid side chains) on the antibody molecule. See *Scientific Foundations of Clinical Biochemistry*, Vol. 1, pp. 202 et seq, (1978). The resulting monoclonal antibody-bearing solid phase is contacted with disruptates of CMV infected cells or cell-free CMV isolates under reducing conditions using pH, ionic strength, temperature, (typically physiological) and residence times that permit the 86,000 dalton protein in the .disruptate to bind to the immobilized monoclonal antibody. The cells or viruses may be disrupted by sonication, lysing or other methods. The solid phase is separated from the diSruptate after the incubation and washed with buffer to remove residual unbound disruptate. The protein is eluted from the solid phase by passing an elutant that dissociates hydrogen hydrogen bonds through the bed. Bases that lower the pH to below about 3 or NaCl solutions above about 2 M are commonly used elutants.

D. Immunoassays Using CMV Proteins

The protein or a derivative thereof may be used to detect the presence of human CMV neutralizing antibodies in samples (e.g., sera) of human Ig-containing body fluids. This procedure might be used, for instance, to identify potential donors of anti-CMV sera for use in passive immunization therapy.

The basic procedure involves incubating the sample with the protein or derivative under conditions that permit antigen-antibody binding and detecting resulting immune complexes that include the protein. The immune complexes may be detected by incorporating a detectable label (e.g., radionuclide, fluorochrome, enzyme) into the complex. A standard solid phase immunoassay procedure is preferred. In such a procedure the protein is immobilized on a solid phase and the immobilized protein is incubated with the sample. The solid phase is then separated from the sample and washed to remove residual, unbound sample. The solid phase is next incubated with a labeled anti-human Ig antibody. Following the second incubation the solid phase separated from the labeled reagent and washed to remove residual unbound labeled reagent. Immune complexes containing anti-CMV antibodies are detected via the label. The complexes may be detected on the surface of the solid phase or eluted from the solid phase. In the case of radionuclides, the immune complexes are normally detected by scintillation scanning. Fluorescent labels are detected by exposing the analyte to excitation energy and detecting the resulting fluorescence. Enzyme labels are detected by incubating the solid phase with an appropriate substrate solution and detecting enzyme activity by spectrophotometric analysis of the substrate solution.

E. CMV Prophylaxis Using Protein

Vaccines based on the protein or a derivative thereof will contain an amount of the protein or derivative thereof that is sufficient to stimulate production of CMV neutralizing antibody admixed with a pharmaceutically acceptable parenteral vehicle. The protein or derivative may, if desired, by coupled to a carrier protein such as keyhole limpet hemocyanin, ovalbumin, or serum albumin. The parenteral vehicle is inherently nontoxic and nontherapeutic. Examples of such vehicles are water, saline, Ringer's solution, dextrose solution and Hank's solution. If desired the vaccine composition may include immunopotentiating agents ( i.e., adjuvants) such as Freund's adjuvant or alum. The amount of protein or derivative administered per inoculation will usually be in the range of about 5 to 50 µg/kg body weight. Such inoculation of animals may also be used to produce anti-CMV sera for use in isolating the protein or for passive immunization.

F. Example

The following example is intended to further illustrate the invention. It is not intended to limit the invention in any manner. The example describes: the preparation of a murine monoclonal antibody that binds specifically to the 86,000 dalton CMV protein; isolation of the protein using the monoclonal antibody; characterization of the protein; and use of the protein as an immunizing agent.

Monoclonal Antibody Preparation

The viruses used in the studies were as follows.

Human CMV strain AD169 was obtained from S. St. Jeor (University of Nevada). Laboratory strains (Towne, Davis) and clinical isolates from congenitally infected newborn infants were provided by J. Waner (University of Oklahoma). Viruses were grown in cultures of human embryonic lung (HEL) fibroblasts with Dulbecco's minimal essential medium (DME medium) supplemented with 1% fetal calf serum. Cell-free infectious virus stocks that contained $10^6$ plaque-forming units (pfu)/ml for laboratory strains and $10^2$ to $10^4$ pfu/ml for clinical isolates were prepared by sonication of infected cells. Antigen was prepared by pelleting virus from the supernatant of roller bottles (490 cm$^2$) of CMV-infected cells showing 90% cytopathic effect. Approximately 100 ml of supernatant with $10^6$ pfu/ml was clarified at 800×g for 10 min, then centrifuged for 1 hr at 200,000 x g.

Female BALB/c weanling mice were immunized with a CMV pellet obtained as described above. Before immunization, the virus pellet in 1 ml of Tris/saline/EDTA was emulsified in 1 ml of Freund's complete adjuvant. Mice were injected intramuscularly with a total of 0.8 ml of this viral emulsion. Four weeks later the mice were given an intraperitoneal injection of 0.5 ml of vital emulsion without adjuvant. After 3 more days, spleens were removed for fusions. At this time the mice had a serum neutralizing-antibody titer of 1:128 by microneutralization assay (described below).

Myeloma cell line P3 x 63AG-8, resistant to 8-azaguanine, was used as a fusion partner for hyperimmune mouse spleen cells. The fusion method was as described by Oi and Herzenberg, (1980) in *Selected Methods in Cellular Immunology*, eds Mishell, B. B. and Shiigi, S. M. (Freeman, San Francisco) pp. 351-372, with a mixture of myeloma and spleen cells at a 1:2 ratio. Medium for all. hybridoma cultures was DME medium supplemented with 18% fetal calf serum, 9% NCTC 109 (M. A. Bioproducts, Rockville, Md.), 450 µM sodium pyruvate, 5 units of bovine insulin per ml, and 1 mM oxaloacetic acid. Hybridoma cells were selected 1 day after the fusion by addition of HAT medium (DME medium with 0.1M hypoxanthine, 0.01 µM aminopterin, and 0.03 µM thymidine). Clones were visible after approximately two weeks.

Hybridoma supernatants were screened initially for CMV binding antibody by sol id phase RIA. The pelleted virus was resuspended in 1 ml of Tris/saline/EDTA (0.05M Tris/0.15M saline/0.001M EDTA, pH 7.4) and diluted 1:100 in the same buffer for binding to plates. Bound antibody was detected with iodinated goat anti-mouse IgG and IgM. Five hundred clones that secreted antibody were detected.

A microneutralization assay was used for rapid screening of the 500 hybridoma clones that produced CMV binding antibody. CMV, antibody, and guinea pig complement (GIBCO) to a final concentration of 2% were incubated for 45 rain at 37° C. Virus-antibody mixture (0.2 ml) was applied to monolayers of HEL cells, seeded the day before at a concentration of $5 \times 10^3$ cells per well in 96-well tissue culture microtiter plates. Medium was changed 1 day later to DME medium with 1% fetal calf serum; 7 days later each well was read microscopically for CPE as compared to control wells with virus alone. Only supernatants that totally inhibited the development of CPE were considered to have neutralized the virus. Eighty-seven hybrids produced neutralizing antibody as measured by microneutralization. Thirty-three were selected for subcloning by limiting dilution. Two stable hybrid clones, 1G6 and 7E4, were derived from two separate parent hybridomas and produced neutralizing antibody in virtually 100% of progeny subclones.

Immunoprecipitation tests were carried out as follows to identify the CMV protein bound by the antibodies produced by 1G6 and 7E4. Radioactive antigen was prepared from CMV monolayers infected (MOI=0.1) and labeled with $^{35}$S-methionine (New England Nuclear; specific activity, 1058 Ci/mmol, 1 Ci=37 GBq). A 4 hr pulse of 500 to 1000 µCi in DME medium without methionine was used per 75-cm$^2$ tissue culture flask. Cell extracts were prepared by lysing $10^7$ washed cells with 1 ml of immunoprecipitation buffer (140 mM NaCl/20 mM Tris-HCl, pH 7.6/1% (vol/vol) Nonidet P-40/0.5% sodium deoxycholate/1 mg of ovalbumin per ml). The supernatant was clarified by centrifugation at 100,000×g for 1 hr at 4° C. and stored at −70° C. Antigen-antibody reactions for immunoprecipitation were carried out at 4° C. for 30 min. Immunoprecipitates were analyzed by SDS-PAGE. Linear 7.5% polyacrylamide gels crosslinked with N,N'-methylenebisacrylamide were used. SDS/PAGE gels were fixed in ethanol/acetic acid/water, 6:1:13 (vol/vol), and prepared for fluorography. Exposure to film was for 5-7 days at −70° C. The apparent molecular masses of CMV proteins were determined from the plot of their migration in SDS/PAGE relative to that of standard $^{14}$C-methylated protein markers ranging from 200,000 to 30,000 daltons (Amersham).

The antibodies from both clones precipitated an 86,000 dalton protein. In view of this one clone, 1G6, was selected for further propagation and testing. Clone 1G6 was injected ip at $10^6$ cells in pristane-primed BALB/c female mice. Ascites fluid was collected 7-14 days after inoculation. Immunoglobulin was isolated from the fluid using ammonium sulfate precipitation. Its subclass and chain type were determined to be IgG2a, Kappa. The 1G6 antibody precipitated 86,000 dalton protein from all strains of CMV mentioned above.

A sample of hybridoma 1G6 was deposited at the American Type Culture Collection on 14 August 1984 and was assigned accession no. HB8599. This deposit was made under the provisions of the Budapest Treaty and will be maintained and made available in accordance with the provisions thereof.

Quantitative virus Neutralization by 1G6 Monoclonal Antibody

Figure 1:
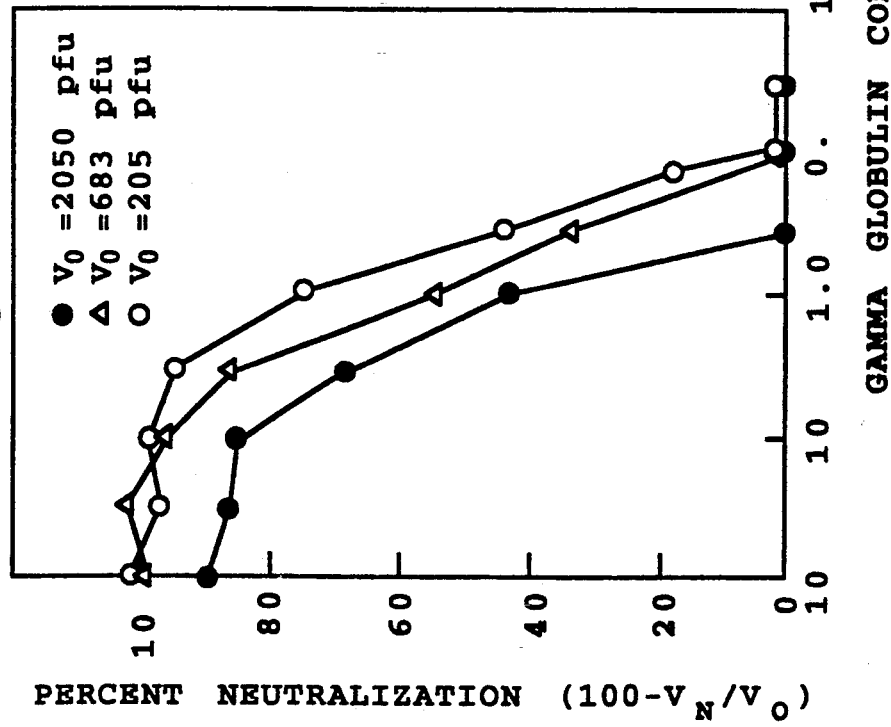

Plaque reduction assays were run as follows. Twenty-four well tissue culture multidishes were seeded with $5 \times 10^4$ HEL cells per well and used after 5 days. Mixtures of CMV ($V_o=205$ pfu, 683 pfu, 2050 pfu) and 1G6 antibody at various concentrations, with an without (only at $V_o=205$) a final concentration of 2% guinea pig complement (gpc) were incubated for 45 rain at 37° C. The virus-antibody mixture, 0.2 ml, was adsorbed for 1 hr to monolayers. Cells were overlaid with DME medium containing 0.5% agarose and 5% fetal calf serum. Seven days later the overlay was removed, monolayers were stained with May-Grunwald-Giemsa solution, and the plaques were counted under a dissecting microscope. The results using CMV AD169 are reported in FIGS. 1 and 2. Percent neutralization was assessed by plaque reduction ($V_n$) and is reported as $100-V_n/V_o$. As shown, neutralization of the challenge virus dose was initiated at 0.1 to 1 $\mu$g/ml. FIG. 2 shows that virus ° neutralization was essentially equivalent with and without gpc.

Table 1 below shows the plaque reduction titers of 1G6 antibody against the six virus strains mentioned above.

TABLE 1

| CMV strain | Tissue culture passage | pfu in neutralization assay ($V_o$) | Ig for 50% reduction of $V_o$, $\mu$g/ml |
|---|---|---|---|
| AD169 | >100 | 60 | 8 |
| Towne | >150 | 2000 | 3 |
| Davis | >58 | 2000 | 3 |
| To | 8 | 30 | 3-11 |
| Wh | 8 | 33 | 8 |
| Wo | 7 | 40 | 100 |

ANALYSIS OF BIOSYNTHESIS OF 86,000 DALTON PROTEIN

CMV-infected cells (MOI=0.1) were labeled with 1000 $\mu$Ci of $^{35}$S-methionine for 4 hr on days 3, 5, and 7 after infection, extracted for antigen (as above) and immunoprecipitated with 3000 $\mu$g of 1G6 antibody (as above). Immunoprecipitation bands in the region of 86,000 daltons were detectable in extracts of cultures labeled on day 3 but showed the greatest intensity on days 5 and 7.

CMV-infected cells were also incubated between days 3 and 7 with 500 $\mu$Ci of $^{35}$S-methionine in DME medium with 10% of the normal methionine concentration, harvested on day 7 after infection, extracted and immunoprecipitated. The predominant protein was still in the 86,000 dalton region.

CMV-infected cultures were pulsed with 1 mCi $^{35}$S-methionine for 15 rain then chased with unlabeled methionine. Cultures were extracted and immunoprecipitated at 15 rain intervals after initiation of the chase. The labeled 86,000 dalton protein remained detectable throughout the experiment indicating it is probably a single gene product.

Immunofluorescent staining of CMV AD169-infected HEL cells incubated with 1G6 antibody were carried out. Specific immunofluorescence was visible in cells stained 48 hr after infection. The pattern was juxtanuclear in the cytoplasm at that time. Between 3 and 6 days, the staining became diffuse throughout the cytoplasm.

AFFINITY CHROMATOGRAPHY OF 86,000 DALTON PROTEIN

Purified IgG derived from 1G6 hybridoma-induced ascites fluid was coupled to cyanogen bromide-activated Sepharose 4B beads according to the manufacturer's instructions (Pharmacia Fine Chemicals, Piscataway, N.J.. A detergent-extracted lysate of CMV-infected cells (1 ml/$10^7$ infected cells) was mixed with the antibody-bead conjugate in a ratio of 5 ml antigen extract to 100 λ of beads. After incubation for two days at 4° C. the 86,000 dalton polypeptide was eluted with ethylene glycol from the antibody-bead conjugate. Purity of the polypeptide was verified by SDS-PAGE.

IMMUNIZATION OF GUINEA PIGS

Two female Hartly strain guinea pigs were immunized with 1 ml of an emulsion of noneluted beads from the antigen-treated column (above) in complete Freund's adjuvant and boosted with a similar dose at 3 weeks. The animals were bled 1 week after the boost.

Immunoprecipitation tests of the sera from the animals showed the sera contained antibodies that bound to the 86,000 dalton protein. Virus neutralization tests of heat-treated sera (to inactivate complement) showed the sera had virus neutralizing titers of greater than 1:64.

Modifications of the above described modes for carrying out the invention that are obvious to those of skill in the fields of virology, protein chemistry, immunology, medicine, or related fields are intended to be within the scope of the following claims.

We claim:

1. A method of isolating from CMV infected cells, or extracellular CMV virions, a purified human CMV protein (i) having a molecular weight of approximately 86,000 daltons as measured by SDS-PAGE; (ii) having in vivo immunizing activity, as evidenced by the capability of eliciting an in vivo neutralizing immune response;; (iii) being substantially free of other CMV proteins and (iv) having an epitope that specifically binds to monoclonal antibody IG6, said method comprising:

(a) disrupting the cells or virions (b) contacting the disruptate with a monoclonal antibody or antiserum that binds specifically to the protein and is immobilized on a solid phase under conditions that permit antigen-antibody binding;

(c) separating unbound disruptate from the solid phase; and (d) eluting the protein from the immobilized monoclonal antibody or anti serum.

2. A method of determining the presence of human CMV neutralizing antibodies in a sample of human serum comprising:

incubating the sample with a purified human CMV virion protein (i) having a molecular weight of approximately 86,000 daltons as measured by SDS-PAGE; (ii) having in vivo immunizing activity, as evidenced by the capability of eliciting an in vivo neutralizing immune response; (iii) being substantially free of other CMV proteins; and (iv) having an epitope that specifically binds to monoclonal antibody IG6, under conditions that permit antigen-antibody binding; and detecting the presence of immune complexes in the incubate.

3. The method of claim 2 wherein the protein is immobilized on a solid phase and step (b) includes incubating the solid phase product of step (a) with a labeled anti-human Ig antibody and detecting the presence of labeled immune complexes on the surface of the solid phase or in an eluate therefrom.

4. A continuous murine cell line capable of producing a monoclonal antibody that binds specifically to a purified human CMV virion protein (i) having a molecular weight of approximately 86,000 daltons as measured by SDS-PAGE; (ii) having in vivo immunizing activity, as evidenced by the capability of eliciting an in vivo neutralizing immune response; (iii) being substantially free of other CMV proteins; and (iv) having an epitope that specifically binds to monoclonal antibodies IG6 and 7EA, said cell line consisting essentially of a fused cell hybrid of:

(a) a cell that produces said antibody; and
(b) a myeloma cell that produces homogeneous immunoglobulin in the hybrid.

* * * * *